(12) United States Patent
Crosby et al.

(10) Patent No.: US 7,875,299 B2
(45) Date of Patent: *Jan. 25, 2011

(54) COMPOSITIONS AND METHODS FOR ENHANCING OR TREATING FEMALE SEXUAL RESPONSE

(75) Inventors: Martin G. Crosby, Charleston, SC (US); Robert M. Bennett, Charleston, SC (US)

(73) Assignee: Semprae Laboratories, Inc., South Orange, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 10/834,162

(22) Filed: Apr. 29, 2004

(65) Prior Publication Data
US 2004/0202739 A1 Oct. 14, 2004

(51) Int. Cl.
*A01N 65/00* (2009.01)
(52) U.S. Cl. .................................................. 424/725
(58) Field of Classification Search ................. 424/724
See application file for complete search history.

(56) References Cited

U.S. PATENT DOCUMENTS

| | | | |
|---|---|---|---|
| 3,886,287 A * | 5/1975 | Kobayashi et al. ......... 514/789 |
| 4,076,854 A * | 2/1978 | Light et al. ................ 426/538 |
| 4,093,708 A | 6/1978 | Zaffaroni |
| 4,134,986 A | 1/1979 | Bajwa |
| 4,317,447 A | 3/1982 | Williams |
| 4,323,548 A | 4/1982 | Scherm |
| 4,393,871 A | 7/1983 | Vorhauer |
| 4,475,916 A | 10/1984 | Himmelstein |
| 4,749,707 A | 6/1988 | Calvo |
| 4,835,138 A | 5/1989 | Alexander |
| 4,858,624 A | 8/1989 | Shihata |
| 4,873,078 A * | 10/1989 | Edmundson et al. ......... 424/64 |
| 4,989,618 A | 2/1991 | Shihata |
| 4,999,351 A | 3/1991 | Kosley |
| 5,077,274 A * | 12/1991 | Evers et al. ................. 512/15 |
| 5,084,277 A | 1/1992 | Greco |
| 5,093,336 A | 3/1992 | Kosley |
| 5,145,855 A | 9/1992 | Kosley |
| 5,177,207 A | 1/1993 | Kosley |
| 5,206,241 A | 4/1993 | Khandelwal |
| 5,207,232 A | 5/1993 | Shihata |
| 5,310,556 A * | 5/1994 | Ziegler ....................... 424/401 |
| 5,350,864 A | 9/1994 | Seamon |
| 5,380,757 A | 1/1995 | Horrobin |
| 5,393,528 A | 2/1995 | Staab |
| 5,529,782 A | 6/1996 | Staab |
| 5,565,466 A | 10/1996 | Gioco |
| 5,614,208 A | 3/1997 | Horrobin et al. |
| 5,690,947 A * | 11/1997 | Habif et al. ................ 424/401 |
| 5,698,589 A | 12/1997 | Allen |
| 5,731,339 A | 3/1998 | Lowrey |
| 5,789,439 A | 8/1998 | Hosono |
| 5,795,591 A | 8/1998 | Lee |
| 5,840,685 A | 11/1998 | Fujii |
| 5,877,216 A | 3/1999 | Place |
| 5,891,915 A | 4/1999 | Wysor |
| 5,945,117 A | 8/1999 | El-Rashidy |
| 5,958,926 A | 9/1999 | Garvey |
| 5,981,563 A | 11/1999 | Lowrey |
| 6,007,824 A | 12/1999 | Duckett |
| 6,036,977 A | 3/2000 | Drizen |
| 6,046,240 A | 4/2000 | See |

FOREIGN PATENT DOCUMENTS

| | | |
|---|---|---|
| CN | 1097311 | 1/1995 |
| CN | 1104886 | * 7/1995 |
| CN | 1237413 | * 12/1999 |
| EP | 222413 | 5/1987 |
| FR | 2777179 | * 10/1999 |
| JP | 405194179 | * 8/1993 |
| JP | 08333266 | * 12/1996 |

(Continued)

OTHER PUBLICATIONS

Revilla et al., *Comparison of Several Procedures Used for the Extraction of Anthocyanins from Red Grapes*, Agric. Food Chem (1998) 46, Previously Presented. 4592-4597.

(Continued)

*Primary Examiner*—Michael V Meller
(74) *Attorney, Agent, or Firm*—Pepper Hamilton LLP

(57) ABSTRACT

The present invention relates to compositions, articles of manufacture, methods of preparation thereof, methods of use thereof, etc., for enhancement of sexual pleasure, conditions, disorders, and diseases related to reproductive physiology and systems, especially of mammalian females. For instance, the present invention relates to all aspects of modulating the female sexual response, including female sexual dysfunction, such as female sexual arousal disorders (FSAD), orgasmic disorders, and sexual pain disorders, and enhancing female sexual pleasure and satisfaction of the female sexual experience. Accordingly, the present invention relates to compositions comprising botanical extracts, active agents, etc., which are useful to treat or affect any of the aforementioned conditions. For example, the present invention relates to a composition, preferably for topical or local use, which comprises one or more of the following ingredients, including, but not limited to, borage seed oil, *Angelica pubescens* root and other *angelica* species, *Coleus forskohlii* extract, vinpocetine, ferulic acid, magnesium, ascorbyl palmitate, capric/caprylic triglyceride, silica, and equivalents thereof.

11 Claims, No Drawings

FOREIGN PATENT DOCUMENTS

| WO | WO 9102516 | * | 3/1991 |
|----|------------|---|--------|
| WO | WO 00/16752 |  | 3/2000 |
| WO | WO 00/69406 | * | 11/2000 |

OTHER PUBLICATIONS

*The Wealth of India*, vol. II, C.S.I.R., India, 1950, p. 308.

*Current Medical Diagnosis*, Tierney et al., Eds., 1997, e.g., pp. 962-965.

*Human Physiology*, Vander et al., Fifth Edition, McGraw-hill Publishing Company, 1990, e.g., p. 628.

Tungler et al., *J. Mol. Catalysis*, 108:45-152, 1996.

Szabo et al., *Arch Pharm.*, 316:629-638, 1983.

* cited by examiner

COMPOSITIONS AND METHODS FOR ENHANCING OR TREATING FEMALE SEXUAL RESPONSE

RELATED APPLICATIONS

This application claims the benefit of U.S. Provisional Application Ser. No. 60/214,472, filed Jun. 27, 2000 and U.S. patent application Ser. No. 09/891,526, filed Jun. 27, 2001, now U.S. Pat. No. 6,737,084, which are hereby incorporated by reference in its entirety.

DESCRIPTION OF THE INVENTION

While increased understanding of the pathophysiology of male erectile dysfunction progressed rapidly in the past decade and led to new therapeutic modalities, little has been done to address similar issues in women. Accordingly, the present invention relates to all aspects of modulating the female sexual response, including female sexual dysfunction, such as female sexual arousal disorders (FSAD), orgasmic disorders, and sexual pain disorders, and enhancing the female sexual experience. In particular, the present invention relates to compositions, articles of manufacture, methods of preparation thereof, methods of use thereof, etc., for conditions, disorders, and diseases related to female reproductive physiology systems, especially those involved in the female sexual response.

Compositions comprising botanical extracts, active agents, etc., can be produced and used in accordance with the present invention that are useful to treat or affect the female sexual response. For example, the present invention relates to compositions, preferably for topical or local use, which comprise one or more of the following ingredients, including, but not limited to, borage seed oil and other sources of gamma linolenic acid (GLA), *Angelica pubescens* root, *Coleus forskohlii* extract, vinpocetine, and other naturally-occurring cyclic adenosine monophosphate (cAMP) and cyclic guanine monophosphate (cGMP) phosphodiesterase (PDE) inhibitors and equivalents thereof. The compositions can produce one or more of the following pharmacological effects, including, but not limited to, increases in localized nitric oxide, cAMP production and/or elevation, cGMP production and/or elevation, prostaglandin $E_1$ production, inhibition of prostaglandin $E_1$ breakdown, calcium channel antagonism, phosphodiesterase inhibition, anti-oxidation, vasodilation, smooth muscle relaxation, etc.

A useful composition in accordance with the present invention can comprise borage seed oil or other borage plant parts, preferably from *Borago officianalis*. The borage plant (e.g., leaves, roots, and seeds) comprises a complex mixture of defined and undefined constituents, including, e.g., acetic acid; alkaloids; allantoin; amabiline; arabinose; ascorbic-acid; beta-carotene; bornesitol; calcium; choline; cobalt; dhurrin; fat; fiber; galactose; gamma linolenic acid; glucose plant; intermedine; lycopsamine; magnesium; malic acid; mucilage; niacin; phosphorus potassium; protein; pyrrolizidines; resin; riboflavin; rosmarinic acid; silicic acid; sodium; supinine; supinine viridiflorate; thiamin and zinc. A preferred bioactive ingredient of Borage is gamma linolenic acid (GLA) having a molecular weight of 278. GLA is a polyunsaturated fatty acid (PUFA) belonging to the group of fatty acids called omega-6 or N-6 fatty acids because of the presence of a double bond between the 6th and 7th carbon. GLA is found predominantly in the seed of the Borage plant, but is also found in evening primrose seed oil and other botanical and natural sources.

Borage seed oil can be prepared by any suitable method, preferably methods which extract GLA and other bioactive agents, such as cold pressure extraction, screw pressure extraction, solvent extraction, supercritical fluid extraction, etc. A borage seed oil can comprise any amount of GLA, preferably, e.g., by weight, at least about 10%, 15%, 20%, 25%, 30%, etc. The oil preferably is free of compounds which are toxic, or deleterious to mammals, such as alkaloids, pyrrolizidine, etc.

Borage seed oil can be present in a composition of the present invention in any effective amount, e.g., 1-100%, 10-95%, 20-95%, 30-95%, 50-95%, 70-90%, 60-90%, 80%, 81%, 82%, 83%, 84%, 84.25%, 85%, 86%, 87%, etc., w/w (i.e., weight of ingredient/weight of total composition).

In addition to borage seed oil, other sources of GLA can be utilized, including, e.g., purified or isolated GLA, botanical extracts, such as evening primrose oil (e.g., *Oenothera biennis* and *Oenothera lamarckiana*), black currant oil, spirulina, oils from the seeds of the Ribes family, etc.

Borage seed oil has a variety of beneficial effects and activities, including, but not limited to, e.g., inhibiting platelet aggregation, lowering blood pressure, anti-inflammatory activity, vasodilation, prostaglandin promoting activity, $PGE_1$ promoting activity (see, below), promoting circulating hormones, causing smooth muscle relaxation, etc. Borage seed oil can be included in a composition of the present invention in amounts which are effective to achieve one or more of the aforementioned effects.

A composition of the present invention can also comprise *Angelica*, such as *Angelica archangelica*, *Angelica sinensis*, *Angelica sylvestris*, *Angelica officinalis*, archangel, European angelica, garden angelica, *Angelica acutiloba*, preferably *Angelica pubescens* which is also known as Du Huo or Du Huo Radix. *Angelica* root is preferred, but other parts of the plants can be used as well. *Angelica* contains a wide and complex variety of different constituents, of a defined and undefined nature. Preferred bioactive compounds are flavinoids, flavones and coumarins, preferably, osthole or 7-methoxy-8-(3-methylpent-2-enyl)coumarin, and alpha-angelica-lactone. Other coumarins, include, e.g., meranzin hydrate, nodakentin, marmesinin, columbianadin, columbianetin, bergapten, heramandiol, 6-alkylcoumarins, angelol-type coumarins, byak-angelicin, ferulin, oxypeucedanin, umbelliprenin, imperatorin, neobyakangelicin, prenylcourmarins, glabralactone, anpubesol, angelical, angelin, furanocourmins, and derivatives thereof. Other bioactive agents include, e.g., linoleic acid, osthenol, falcarindiol, numerous flavinoids and flavones, 11(S), 16(R)-dihydroxyoctadeca-9Z,17-diene-12,14-diyn-1-yl-acetate, xanthotoxin, umbelliferone, ferulic acid, magnesium, and derivatives thereof.

*Angelica* possesses a number of pharmacological activities, including, but not limited to smooth muscle relaxant activity, phosphodiesterase inhibition, calcium antagonist activity, cycloxygenase and 5-lipoxygenase inhibition (e.g, Liu et al., *Pharm. Bio.*, 36(3):207-216, 1998), etc. Coumarins, and osthole in particular, have been identified to display activities such as, inhibition of platelet aggregation, inhibition of smooth muscle contraction, smooth muscle relaxation (e.g., Che-Ming et al., *Naunyn-Schmiedeberg's Arch. Pharmacol.*, 349:202-208, 1994), inhibition of calcium flux, cyclic nucleotide (such as cGMP and cAMP) phosphodiesterase inhibition, increase in cAMP and cGMP levels, anti-proliferative, anti-inflammatory (Yuh-Fung et al., *Planta Medica*, 61(1):2-8, 1995), enhancement of the increase of cAMP and cGMP induced by forskolin, vasorelaxation, neurotransmitter receptor binding, such as GABA, 5HT-1A, D-2, and D-1 receptors (Jyh-Fei et al., *Proceedings of the National*

Science Council Republic of China, Part B, Life Sci., 19(3): 151-158, 1995), etc. Alpha-angelicalactone also possesses various activities, including, e.g., calcium antagonism. See, e.g., Entman et al., J. Clin. Invest., 48:229-234, 1969. Ferulic acid, another component of *Angelica* root also has been shown to scavenge oxygen free radicals and increase intracellular cAMP and cGMP. See, e.g. Zheng R L, Zhang H., *Free Radic Biol Med.*, 22(4):581-586, 1997. Preferred activities of *Angelica* are cyclic nucleotide phosphodiesterase inhibition, calcium antagonism, oxygen free radical scavenging, smooth muscle modulation, as either vasorelaxant or vasodilatory.

A composition of the present invention can comprise any effective amount of *Angelica*, preferably *Angelic pubescens* root, e.g., 0.1-99%, 0.1-80%, 0.1-50%, 0.5-8%, 1%, 2%, 3%, 4%, 5%, etc. w/w.

In another embodiment of the present invention, a composition can further comprise *Coleus forskohlii*, preferably from its tuber or roots. The plant is a member of the Labiatae family and grows as a perennial. It is native to India, Nepal, Sri Lanka, and Thailand. See, e.g., *The Wealth of India*, Vol. II, C.S.I.R., India, 1950, Page 308. *Coleus forskohlii* comprises a diverse and complex mixture of compounds, e.g., diterpenes, and derivatives thereof. A preferred bioactive diterpene compound is forskolin and related diterpenes.

*Coleus forskohlii* can be utilized in any form which is effective, including, but not limited to dry powders, grounds, emulsions, creams, extracts, and other conventional formulations. Extracts can be prepared routinely, e.g. by contacting the plant parts with a suitable solvent to extract a diterpene or other compound from the material (e.g., see, U.S. Pat. No. 4,118,508, JP 11292777, and JP 6133731 for extraction processes). Any amount of *Coleus* which is effective can be utilized in compositions of the present invention, e.g., at least about 0.1-99%, 0.1-80%, 0.1-50%, 0.5-8%, 1%, 2%, 3%, 4%, 5%, etc. w/w of an 80% extract.

*Coleus forskohlii*, particularly forskolin and related diterpenes, have a number of biological activities, including, smooth muscle relaxation, adenylate cyclase stimulation, elevation of levels of cAMP, anti-inflammatory, ant-spasmodic, etc. Since forskolin and related diterpenes stimulate adenylate cyclase, resulting in the production of the second messenger cAMP, any biological process mediated by cAMP can therefore be stimulated by administration of *Coleus forskohlii*.

Compositions of the present invention can also comprise vinpocetine (eburnamenine-14-carboxylic acid ethylester) and derivatives thereof. Vinpocetine is a naturally-occurring product found, e.g., in vinca minor (periwinkle). It can be extracted from natural sources, such as vinca, or produced synthetically. Various derivatives of vinpocetine can be utilized, including salts. For methods of synthesis of vinpocetine and derivatives, e.g., U.S. Pat. No. 4,035,370; Szabo et al., *Arch. Pharm.*, 316:629-638; Tungler et al., *J. Mol. Catalysis*, 108:45-152, 1996; U.S. Pat. No. 4,749,707 (e.g., citrate and phosphate salts). Vinpocetine and its derivatives have various activities and effects, including, e.g., phosphodiesterase inhibition, selective PDE type I inhibition, vasodilation activity, smooth muscle relaxation, increases in levels of cAMP and/or cGMP. etc.

Any amount of vinpocetine which is effective can be utilized in compositions of the present invention, e.g., at least about 0.1-99%, 0.1-80%, 0.1-50%, 0.5-8%, 1%, 2%, 3%, 4%, 5%, etc.

In addition to the above-mentioned botanical extracts, or as an alternative thereof, a composition of the present invention can comprise any agent which possesses one of more of the biological activities associated with said botanical extracts.

For example, the present invention also relates to agents having "$PGE_1$ promoting activity." As mentioned, one of the major constituents of borage seed oil is GLA. GLA is a precursor of prostaglandin E1 ($PGE_1$), a potent biological effector molecule. $PGE_1$ has many physiological effects. While not wishing to be bound to any theory, it is believed that at least some of the beneficial effects produced by borage seed oil is mediated by its delivery of a precursor to the $PGE_1$ metabolic pathway, thereby stimulating production of $PGE_1$. Thus, any compound, mixtures thereof, compositions, botanicals, etc. which comprise a $PGE_1$ or a $PGE_1$ precursor can be characterized as having "$PGE_1$ promoting activity," e.g., causing the production of $PGE_1$, or possessing $PGE_1$ activity.

Another useful class of agents in accordance with the present invention are those which elevate levels of cyclic nucleotides, such as cAMP and cGMP, e.g., by inhibiting phosphodiesterases which hydrolyze the cyclic nucleotides, by stimulating adenylate cyclase, or receptors coupled thereto, by acting on G-proteins, etc. In accordance with the present invention, any amount of elevation or increase of cyclic nucleotide which is effective to elicit a desired result, such as treating FSD, enhancing sexual arousal, etc. Amounts of increase as compared to normal can be at least 5%, 10%, 50%, 75%, 90%, 1-fold, 2-fold, 5-fold, 10-fold, 20-fold, etc. These increases can be sudden, transient over a few minutes, localized, etc., as long as the desired effect is achieved, e.g., modulating the female sexual response.

Elevation of levels of cyclic nucleotides can be accomplished by cyclic nucleotide phosphodiesterase (PDE) inhibition. There are a number of different cyclic nucleotide phosphodiesterase isoenzymes, including types I, II, III, IV, V, VI, and VII. See, e.g., Nicolson et al., 1991. PDE inhibitors can be non-selective (e.g., theophylline or caffeine), or selective for one or more PDE isoenzymes. Selective inhibitors, include, I (vinpocetine), III (milrinone, amrinone, pimobendan, cilostamide, enoximone, peroximone, vesnarinone), IV (rolipram, R02-1724), and V (zaprinast, dipyridamole). Other useful PDE inhibitors include compounds disclosed in U.S. Pat. No. 5,958,926.

In addition to elevating levels of cAMP through inhibition of PDEs (e.g., utilizing *Angelica pubsescens* root extract and other species of *Angelica*) cAMP levels can be elevated by directly stimulating adenyate cyclase and causing synthesis of cAMP, e.g., using *Coleus forskohlii*, and derivatives thereof. Useful forskolin derivatives, and their synthesis, are disclosed in, e.g., EP 222,413, U.S. Pat. Nos. 5,789,439, 5,350,864, 5,206,241, 5,177,207, 5,145,855, 5,093,336, 4,999,351, and 4,134,986.

Compositions can be administered in any form by any effective route, including, e.g., oral, parenteral, enteral, intraperitoneal, topical, local, dermal, transdermal, ophthalmic, nasally, nasopharyngeal absorption, local, topical, non-oral, aerosal, inhalation, subcutaneous, intramuscular, buccal, sublingual, rectal, vaginal, intra-arterial, rapid infusion, intravenously, long-release implants, etc.

In preferred embodiments of the invention, compositions are administered to the external female genitalia and/or vaginally, e.g., as a vaginal cream, foam, gel, jelly, liquid, emulsion, solution, suspension, cream, spray, powder, suppository, tablet, device, etc. For example, a composition can be preferably applied to the female external genitalia, such as the mons pubis, labia majora and minora, hymen, clitoris, prepuce of the clitoris, vestibule of the vagina, and/or vestibular glands. The external genitalia is also called the vulva or pudendum. Compositions can also be applied to the internal wall of the vagina, e.g., to the adventia, muscularis, mucosa, and rugae.

A composition of the present invention can also be administered by or in the form of a device, such as a cartridge, diaphragm, female mechanical barrier-type device, feminine cap (e.g., U.S. Pat. Nos. 4,858,624, 4,989,618, and 5,207,232), film, intrauterine barrier-type device, sponge, tampon, osmotic drug delivery device (e.g., U.S. Pat. Nos. 5,795,591, 4,475,916, and 4,093,708), ring, or sheath. Such devices can carry the composition in any effective manner, e.g., a device can be impregnated or coated with the composition, or fitted with a carrier element, such as a film (e.g., U.S. Pat. No. 5,529,782), or polymeric material, etc., that contains composition. The device can then be inserted into the vagina where delivery is effected. See, e.g., U.S. Pat. No. 4,317,447. A device can be a sponge-like structure, such as a polymeric sponge tampon, which contains a composition of the present invention. See, e.g., U.S. Pat. No. 4,393,871. Such a device can be inserted into the vagina prior to intercourse. The device can also be reusable. In the case of devices, it can be advantageous to formulate the composition with compounds, such as water-soluble polymers or dissolvable materials, which disintegrate in the vaginal fluids, thereby releasing the active agents. Any suitable polymer can be used, e.g., as described in U.S. Pat. Nos. 5,840,685 5,393,528, 5,084,277, 4,835,138, 4,323,548, and 4,322,399.

A composition of the present invention can also be administered by a male condom, e.g., by applying the composition to the condom prior to insertion into the vagina, e.g., in combination with other lubricants, or, as a dry or wet film or coating on the exterior of the condom surface. See, e.g., U.S. Pat. No. 5,954,054.

In general, any delivery means, including devices, polymers, etc., that are used to deliver agents vaginally can be utilized in accordance with the present invention, such as means for delivering antiviral agents, bacteriocides, contraceptives, hormones, spermicides, virucides, lubricants, etc.

Compositions of the present invention can further comprise other active agents, including, e.g., contraceptive agents, spermicidal agents, such as, e.g., nonoxynol-9, octoxynol, menfegol, benzalkonium chloride, peroxygen compounds or hydrogen peroxide (e.g., U.S. Pat. No. 5,778,886), bacteriocides, germicides, antiviral agents, virucides, vasodilators, agents which increase vaginal lubrication (e.g., hydriodic acid syrup as disclosed in U.S. Pat. No. 5,470,588), etc.

In addition, compositions of the present invention can further comprise any agent which enhances the sexual response and/or treat diseases and conditions related to sexual dysfunction. Such agents include, e.g., apomorphine (e.g., U.S. Pat. No. 5,945,117), nitric oxide releasing compounds (e.g., U.S. Pat. No. 5,877,216), ginkgo (e.g., U.S. Pat. No. 5,897,864), hydriodic acid (U.S. Pat. No. 5,470,588), agents disclosed in U.S. Pat. No. 4,521,421.

The compositions of the present invention can further comprise any pharmaceutically acceptable carrier. By the phrase, "pharmaceutically acceptable carrier," it is meant any excipient, solvent, vehicle, inert ingredient, etc., which is formulated with the active ingredients of a pharmaceutical composition, such as the standard agents described, e.g., in *Remington's Pharmaceutical Sciences*, Eighteenth Edition, Mack Publishing Company, 1990. Examples of suitable carriers are well known in the art and can include, but are not limited to, water, phosphate buffered saline solutions, phosphate buffered saline containing Polysorb 80, emulsions such as oil/water emulsion and various type of wetting agents, salt solutions, alcohols, gum arabic, vegetable oils, benzyl alcohols, aqueous vehicles, water-miscible vehicles, nonaqueous vehicles (e.g., corn oil, cottonseed oil, peanut oil, sesame oil, ethyl oleate, isopropyl myristate, and benzyl benzoate), etc. Carriers also include, e.g., milk, sugar, certain types of clay, silica, gelatin, stearic acid or salts thereof, magnesium, magnesium stearate and other forms or salts of magnesium, or calcium stearate, talc, vegetable fats or oils, gums, glycols, propylene glycol, buffers, antimicrobial agents, preservatives, flavor, fragrance and color additives, gelatin, carbohydrates such as lactose, amylose or starch, talc, silicic acid, viscous paraffin, perfume oil, fatty acid monoglycerides and diglycerides, pentaerythritol fatty acid esters, hydroxy methylcellulose and the like. Other additives include, e.g., antioxidants and preservatives, coloring, flavoring and diluting agents, emulsifying and suspending agents, such as acacia, agar, alginic acid, sodium alginate, bentonite, carbomer, carrageenan, carboxymethylcellulose, cellulose, cholesterol, fatty acids, triglycerides and esters of fatty acids, fatty alcohols, gelatin, hydroxyethyl cellulose, hydroxypropyl cellulose, hydroxypropyl methylcellulose, methylcellulose, octoxynol 9, oleyl alcohol, povidone, propylene glycol monostearate, sodium lauryl sulfate, sorbitan esters, stearyl alcohol, tragacanth, xanthan gum, and derivatives thereof, solvents, transdermal enhancers (ethanol, propylene glycol, water, sodium oleate, leucinic acid, oleic acid, capric acid, sodium caprate, capric/caprylic triglyceride, silica, lauric acid, sodium laurate, neodecanoic acid, dodecyl-amine, cetryl lactate, myristyl lactate, lauryl lactate, methyl laurate, phenyl ethanol, hexa-methylene lauramide, urea and derivatives, dodecyl N, N-dimethylamino acetate, hydroxyethyl lactamide, phyophatidylcholine, sefsol-318 (a medium chain glyceride), isopropyl myristate, isopropyl palmitate, palmitic acid, several surfactants, including poly-oxyethylene (10) lauryl ether (Brij 361 R), diethyleneglycol lauryl ether (PEG-2-L), laurocapram (Azone; 1,1-dodecylazacycloheptan-2-one), acetonitrile, 1-decanol, 2-pyrrolidone, N-methylpyrrolidone, N-ethyl-1-pyrrolidone, 1-Methyl-2-pyrrolidone, 1-lauryl-2-pyrrolidone, sucrose monooleate, dimethylsulfoxide (DMSO) about 80% concentration required, decylmethylsulfoxide (n) enhances primarily polar or ionic molecules (soluble in ethanol), acetone, polyethylene glycol 100-400 MW, dimethylacetamide, dimethylformamide, dimethylisosorbide, sodium bicarbonate, various $N_{7-16}$-alkanes, mentane, menthone, menthol, terpinene, D-terpinene, dipen-tene, N-nonalool and limonene, skin penetration enhancers (e.g., lecithin), and miscellaneous ingredients such as microcrystalline cellulose, citric acid, dextrin, dextrose, liquid glucose, lactic acid, lactose, magnesium chloride, potassium metaphosphate, starch, and the like.

As mentioned, compositions of the present invention can comprise one or more of the following ingredients, e.g., borage seed oil, *Angelica pubescens* root, *Coleus forskohlii* extract, magnesium and its salts, ferulic acid, vinpocetine, and equivalents thereof, in any binary, trinary, etc., combination. Such ingredients can be present in synergistic amounts. Examples of topical compositions, include, e.g., binary combinations, such as an effective amounts of borage seed oil, and *Angelica pubescens* root; effective amounts of borage seed oil, and *Coleus forskohlii* extract; effective amounts of *Angelica pubescens* root, and *Coleus forskohlii* extract; and quarternary combinations, such as effective amounts of borage seed oil, *Angelica pubescens* root, *Coleus forskohlii* extract, and vinpocetine. Such compositions can further comprise pharmaceutically-acceptable excipients, skin- and mucosal penetration enhancers, etc. In preferred embodiments, included as excipients are, e.g., de-ionized water (e.g, about 0.5-50%, preferably 5%, concentration), Span 80 (sorbitan monooleate (e.g., 0.2-20%, preferably 2%, concentration), lecithin (e.g., egg or soy phosphatidylcholine (e.g., e.g., 0.2-20%, preferably 2%, concentration), lavendar for body oils by Flavor and Fragrance Specialties (0.05-1.25%, preferably 0.25%), Blackberry Musk for body oils by Flavor and Fragrance Specialties (0.1-2.5%, preferably 0.5%) or other flavors and fragrances, glycerin (e.g., 2-10% w/w), saccharin or other sweetening agents, and monosodium guanosine mono phosphate (flavor enhancer), silica, ferulic acid and other forms of ferulate, magnesium sulfate and other forms of magnesium, vitamine E acetate and other forms of tocopherol, and ascorbyl palmitate and other forms of ascorbic acid along with other anti-oxidants and stability enhancers. Ingredients, and amounts of ingredients, can be adjusted such that the compositions possess minimal irritation to the female reproductive organs. Ingredients can also be included that enhance the cosmetic appeal (e.g., enhancing the smell, feel, etc.) of the compositions, but which are inert as far as enhancing the sexual response, e.g., enhancing the smell, feel, etc., of a composition.

A quarternary topical composition can comprise, e.g., a) borage seed oil and/or evening primrose oil is 10-99% w/w of said composition; b) *Angelica pubescens* is 0.001-99% w/w of said composition, c) *Coleus forskohlii* is 0.001-8% w/w of said composition, and d) vinpocetine is 0.001-8% w/w of said composition. This composition can further comprise, e.g., e) magnesium 0.001-90%, f) ferulic acid 0.001-10%.

The present invention also relates to methods of using any of the mentioned compositions, e.g., for treating or affecting diseases and conditions associated with sexual function, especially associated with the female reproductive system, such as for treating sexual dysfunction, facilitating sexual arousal, enhancing or improving sexual response, or enhancing or improving sexual pleasure, comprising administering an effective amount of a composition in accordance with the present invention. By "sexual functioning," it is meant any activity associated with the genitalia, such as sexual intercourse. The methods are useful to treat various types of female sexual dysfunction (FSD), such as female sexual arousal disorder (FSAD), desire disorders, orgasmic disorders, and sexual pain disorders. Premenopausal and postmenopausal women can be treated.

The stages of female sexual activity include excitement (arousal), plateau, and orgasm. The arousal response is a physiological and psychological process involving, e.g., muscle relaxation, vasocongestion, vasodilation, and muscular contraction. The clitoris which contains a rich supply of sensory endings becomes erect as a result of vasocongestion. During intercourse, the vaginal epithelium becomes highly congested and secretes a mucus-like lubricant which is an exudate. See, e.g., *Human Physiology*, Vander et al., Fifth Edition, McGraw-hill Publishing Company, 1990, e.g., Page 628; *Current Medical Diagnosis*, Tierney et al., Eds., 1997, e.g., Pages 962-965; U.S. Pat. No. 5,958,926, especially Column 7-9. Compositions of the present invention can particularly facilitate and/or enhance arousal and orgasm, e.g., by enhancing associated vasocongestion and vasodilation and sensory input.

Sexual arousal disorders, e.g., inability to become aroused or inability to attain or maintain sufficient sexual excitement, female impotence, vaginismus, frigidity, disorders of sexual desire, e.g., absence of libido, decreased or loss of sensation, etc. can be treated or affected in accordance with the present invention. In addition, sexual pain disorders, such as painful intercourse, or dyspareunia, can be treated. The latter can be caused by a number of factors, including, e.g., endometriosis, vaginismus, insufficient lubrication of the vagina, etc. FSAD can be manifested by a patient as a lack of subjective excitement, a lack of genital lubrication or swelling, or another somatic responses. Disorders of arousal include, but are not limited to, lack or diminished vaginal lubrication, decreased clitoral and labial sensation, decreased clitoral and labial engorgement, lack of vaginal smooth muscle relaxation, and disorders involving hormonal status. Compositions of the present invention can treat any of the mentioned conditions associated with female sexual dysfunction.

In addition, the compositions are useful for enhancing or improving sexual response and/or enhancing or improving sexual pleasure and sensation. By the terms, "enhance" or "improve," it is generally meant that administration of a composition increases the subject's satisfaction with the sexual activity as compared to the activity when in the absence of the composition. This includes, e.g., enhancement of vaginal wetness, warmth, engorgement, sensitivity, sensation, tingling, arousal, orgasm, quicker to arousal, quicker to orgasm, and enhancement of any of the above-mentioned conditions (e.g., clitoral and labial sensation or vaginal smooth muscle relaxation), etc. Any amount of increase in satisfaction can be achieved, including, e.g., 1%, 5%, 10%, 50%, 100%, 2-fold, etc. Satisfaction can be determined by any suitable method, e.g., a survey or questionnaire in which a user is asked to assess, after using a composition of the present invention, changes in the genital area and sexual pleasure.

By the term "administering," it is meant that a composition is delivered to the subject in such a way that it can achieve the desired purpose, e.g., treating a condition or disease associated with sexual function. As mentioned, such composition can be administered by any effective route, preferably vaginally, such as topically or locally. Compositions of the present invention can be administered to any suitable subject, preferably human females, but also to females of other species, such as apes, monkeys, chimpanzees, pets, such as dogs, cats, rats, hamsters, and mice, horses, pigs, cows, sheep, and other domestic animals, and males of any species.

In addition to females having any of the aforementioned conditions, suitable female subjects, include, e.g., females having illnesses that interfere with sexual arousal, such as diabetes mellitus, hypothyroidism, pelvic disorders, neurological disorders (e.g., multiple sclerosis), muscular disorders (e.g., muscular dystrophy), and psychological disorders (guilt, anxiety, depression, fatigue, or interpersonal conflicts), conditions that lead to failure of the vasocongestion response, vaginal dryness, anorgasmic females, intermittently orgasmic females, orgasmic females desiring greater sexual response, sexual-related failures associated with age, neurosis, females having sexual desire disorders, orgasmic dysfunction, drug-induced sexual dysfunction (e.g., associated with oral contraceptives, anti-hypertensives, tranquilizers, SSRI antidepressants), hypoactive sexual desire (HSD), postmenopausal women, etc.

Administration of compositions of the present invention can alleviate, improve, or ameliorate any of the mentioned conditions. In addition, sexual response can be improved, e.g., decreasing foreplay (e.g., the time usually required for a subject to reach arousal), decreasing latency time between orgasms, decreasing the time to reach orgasm, and facilitating orgasm and multiple orgasm.

An effective amount of a composition is administered to a target subject. Effective amounts are such amounts that are useful to achieve the desired effect, preferably a beneficial, pleasurable or therapeutic effect as described above. Such amounts can be determined routinely, e.g., by administering different dosages to subjects and surveying or questioning such subjects after sexual activity about their preferences and the effectiveness of the treatment. Amounts can be selected based on various factors, including the age, health, gender, and weight of the subject.

EXAMPLES

Example 1

Preparation of Base Oil

Freshly milled *Angelica pubescens* root was mixed in a 1:1 weight/weight ratio (other ratios, as described above can be used, e.g., 0.8:1) with borage seed oil (e.g., containing 20-26% GLA content, depending on the specific source). Lavender for Body Oils and Blackberry Musk for Body Oils (obtained from Flavor and Fragrance Specialties) were each added at a concentration of 10 mg/ml. (Optionally, in some cases, primrose oil (e.g., 9% GLA content) was added to the base oil for a final concentration of 1% primrose oil.) This mixture was stirred rapidly in a water-jacketed blender, and heated at 80° C. for a 3-hour period. The resulting finely-divided solid/oil mixture was cooled to room temperature, filtered once through a 20-micron filter, and then refiltered through a 5-micron filter. The base oil mixture was bright gold-colored with a mild odor of *Angelica pubescens*.

Example 2

Preparation of a Gel Composition for Topical Application

A composition was formulated comprising 70% of the base oil produced according to Example 1. To this oil, *Coleus forskohli* (containing about 80% forskolin) was added to the base oil for a final concentration of 10 mg/ml base oil. Vinpocetine was to this at a final concentration of 10 mg/ml base oil.

The following further ingredients were added to the mixture, but are optional ingredients: magnesium sulfate (USP or FCC) at a concentration of 40 mg/ml, capric/caprylic triglyceride (at about 25% w/w) to enhance permeation, ferulic acid from *Angelica* species at 1-20 mg/ml, acorbyl palmitate to stabilize oil and retard oxidation, alpha-tocopherol and tocopherol acetate to stabilize oil and retard oxidation, soy lecithin granular USP or FCC) at a concentration of 1-50 mg/ml of base oil, span 80 (sorbitan monooleate) at 1-10 mg/ml of base oil, fumed silica (at about 4% w/w) to form a gel version of the oil, and saccharin. Propylene glycol can be added to increase lubricity, but were not used in the case examples below.

The above mixture was heated and rapidly stirred in a water bath set at 70° C. for 30 minutes. After cooling to room temperature, the mixture was filtered through once through a 20-micron filter, and then refiltered through a 5-micron filter. The resulting mixture is centrifuged at 11,000 rpm for 5 minutes, and the oil portion is collected. To further clarify the product, the mixture is filtered, under vacuum, through a 5-micron filter, and then placed in an amber glass screw top container and stored at room temperature.

Example 3

Preparation of an Oil Composition for Topical Application

To prepare an oil for topical application, a composition is formulated in accordance with Example 2, but fumed silica is omitted, and optionally capric/caprylic acid, as well.

CASE EXAMPLES

Case Example 1

A multi-parous perimenopausal forty-two year old woman in a monogamous relationship with self-described complaints of difficulty with sexual arousal and difficulty with vaginal lubrication during sex volunteered to use a composition produced according to Example 2. With the consent of her partner, she applied approximately 0.6 mil to her clitoris and labial areas during foreplay. The woman indicated a pleasurable gradual warming sensation to the areas of application. She reported that within five minutes of application, the warming had reached a plateau and that her clitoral sensation was increased. Also her labia began to feel plump or swollen (aroused). She reported no difficulties with lubricating and claimed that sex was much more pleasurable and that her vaginal sensation had increased. Neither her nor her partner reported any adverse effects. Her partner reported that she was clearly more sexually aroused than usual and that her vagina was warmer than usual. Both partners indicated they would try more samples if provided.

Case Example 2

A multi-parous post-menopausal fifty-three year old woman in a monogamous relationship with self-described complaints of decreased clitoral and vaginal sensation volunteered to use a composition produced according to Example 2. With her partner's consent, she applied approximately 0.6 ml to her clitoral and labial areas and applied the remainder of the vial (0.4 ml) to her partner's penis during foreplay. The couple reported approximately ten minutes of foreplay. The woman claimed feeling a gradual warming and heightened sensation of her clitoris and vagina within about five minutes after application. Her partner also noticed a slight warming effect of his penis. The couple reported engaging in intercourse after about ten minutes of foreplay. The woman claimed that the composition significantly improved her sensations during intercourse and overall had increased her sexual satisfaction. Her partner claimed that from the looks (expressions) on her face, she seemed to enjoy his thrusting more than usual. Neither partner reported any adverse effects. Both partners indicated they would regularly use the composition if provided with more samples.

Case Example 3

A monoparous thirty-four year old woman in a monogamous relationship who described herself as sexually normal volunteered to use a composition produced according to Example 2. With the consent of her partner, she applied approximately 0.7 ml to her clitoral and labial areas during foreplay. After about five minutes she reported a pleasurable and gradually building warming sensation that reached a plateau of intensity in about ten minutes. She claimed that the composition made it easier to reach orgasm and made it more intense than usual. She also claimed its pleasurable effects lasted for about forty-five minutes. She reported the composition significantly heightened her sexual experience and would use it regularly if she could get more samples. Neither partner reported any adverse reactions.

Case Example 4

A thirty-eight year old woman volunteered to use 0.5 ml of a composition produced according to Example 2. Using a standardized consumer testing results questionnaire, she reported the following information: a) That sensation and sensitivity in her genital area seemed to be more than usual. b) That it was pleasurable and satisfying. c) That she first noticed the change in sensation in about five minutes. c) That the change in sensation lasted approximately one hour. d) That she experienced enhanced warmth, tingling and arousal. e) That after using the product, intercourse was more pleasurable and satisfying than normal. f) That her vaginal lubrication seemed to be the same as always. g) That her ability to achieve orgasm was unchanged. h) That the product enhanced her sexual experience and would like to continue using it. i) That she would purchase the product and use it on special occasions and when she needed a boost. j) That she did not experience any unpleasant or unwanted effects.

Case Example 5

A thirty year old woman volunteered to use 0.5 ml of a composition produced according to Example 2. Using a standardized consumer testing results questionnaire, she reported the following information: a) That sensation and sensitivity in her genital area seemed to be more than usual. b) That it was pleasurable and satisfying. c) That she first noticed the change in sensation in about two to three minutes. c) That the change in sensation lasted approximately forty minutes. d) That she experienced enhanced wetness, warmth, enhanced fullness (engorgement) and enhanced sensitivity. e) That after using the product, intercourse was more pleasurable and satisfying than normal. f) That her vaginal lubrication seemed to be more than usual. g) That her ability to achieve orgasm was unchanged. h) That the product enhanced her sexual experience and would like to continue using it. i) That she would purchase the product and use it routinely. j) That she did not experience any unpleasant or unwanted effects.

Case Example 6

A forty-four year old woman volunteered to use 0.5 ml of a composition produced according to Example 2. Using a standardized consumer testing results questionnaire, she reported the following information: a) That sensation and sensitivity in her genital area seemed to be more than usual. b) That it was pleasurable and satisfying. c) That she first noticed the change in sensation in four to five minutes. c) That the change in sensation lasted more than one hour. d) That she experienced enhanced wetness, warmth, tingling, sensation, orgasm and quicker to orgasm. e) That after using the product, intercourse was more pleasurable and satisfying than normal. f) That her vaginal lubrication seemed to be more than usual. g) That her ability to achieve orgasm was easier to achieve. h) That the product enhanced her sexual experience and would like to continue using it. i) That she would purchase the product and use it on special occasions and when she needed a boost. j) That she did not experience any unpleasant or unwanted effects.

Case Example 7

A twenty-three year old woman volunteered to use 1 ml of a composition produced according to Example 2. Using a standardized consumer testing results questionnaire, she reported the following information: a) That sensation and sensitivity in her genital area seemed to be more than usual. b) That it was pleasurable and satisfying. c) That she first noticed the change in sensation in a few minutes. c) That the change in sensation lasted approximately thirty minutes. d) That she experienced enhanced warmth, tingling, arousal, sensation, orgasm and quicker to orgasm. e) That after using the product, intercourse was more pleasurable and satisfying than normal. f) That she did not notice a change in her vaginal lubrication, but her partner did. g) That her ability to achieve orgasm was easier to achieve. h) That the product enhanced her sexual experience and would like to continue using it. i) That she would purchase the product and use it when she needed a boost. j) That she did not experience any unpleasant or unwanted effects except for slight irritation.

Case Example 8

A fifty-four year old woman volunteered to use 1 ml of a composition produced according to Example 2. Using a standardized consumer testing results questionnaire, she reported the following information: a) That sensation and sensitivity in her genital area seemed to be more than usual. b) That it was pleasurable and satisfying. c) That she first noticed the change in sensation in two minutes. c) That the change in sensation lasted approximately forty-five minutes. d) That she experienced enhanced wetness, warmth, tingling, sensation, and arousal. e) That after using the product, intercourse was more pleasurable and satisfying than normal. f) That her vaginal lubrication seemed to be more than normal. g) That her ability to achieve orgasm was easier to achieve. h) That the product enhanced her sexual experience and would like to continue using it. i) That she would purchase the product and use it routinely. j) That she experienced some slight burning and soreness. She added that her partner said it made him more sensitive and he had a better climax.

Case Example 9

A fifty year old woman volunteered to use 0.5 ml of a composition produced according to Example 2. Using a standardized consumer testing results questionnaire, she reported the following information: a) That sensation and sensitivity in her genital area seemed to be more than usual. b) That it was pleasurable and satisfying. c) That she first noticed the change in sensation in about five minutes. c) That she did not pay attention to how long the change in sensation lasted. d) That she experienced enhanced wetness, warmth, tingling, sensation and enhanced orgasm. e) That after using the product, intercourse was more pleasurable and satisfying than normal. f) That she did not notice a change in her vaginal lubrication, but her partner noticed. increased lubrication. g) That her ability to achieve orgasm was unchanged. h) That the product enhanced her sexual experience and would like to continue using it. i) That she would purchase the product and use it when she needed a boost. j) That she did not experience any unpleasant or unwanted effects. She also commented that she could not use it regularly because her partner enjoys oral sex.

Case Example 10

A forty-three year old woman volunteered to use 1 ml of a composition produced according to Example 2. Using a standardized consumer testing results questionnaire, she reported the following information: a) That sensation and sensitivity in her genital area seemed to be more than usual. b) That it was pleasurable and satisfying. c) That she first noticed the change in sensation in about ten minutes. c) That the change in sensation lasted approximately one hour. d) That she experienced enhanced wetness, warmth, tingling, sensation, arousal, orgasm and quicker to orgasm. e) That after using the product, intercourse was more pleasurable and satisfying than normal. f) That her vaginal lubrication seemed to be more than usual. g) That her orgasm was easier to achieve. h) That the product enhanced her sexual experience and would like to continue using it. i) That she would purchase the product and use it on special occasions. j) That she did not experience any unpleasant or unwanted effects other than some minor burning and soreness.

Case Example 11

A thirty-eight year old woman volunteered to use 1 ml of a composition produced according to Example 2. Using a standardized consumer testing results questionnaire, she reported the following information: a) That sensation and sensitivity in her genital area seemed to be more than usual. b) That it was pleasurable and satisfying. c) That she first noticed the change in sensation in about ten minutes. c) That the change in sensation lasted approximately two hours. d) That she experienced enhanced warmth, tingling and arousal. e) That after using the product, intercourse was more pleasurable and satisfying than normal. f) That her vaginal lubrication seemed to be the same as always. g) That her ability to achieve orgasm was unchanged. h) That the product enhanced her sexual experience and would like to continue using it. i) That she would purchase the product and use it on special occasions. j) That she experienced some minor burning, but did not feel any product improvements were necessary.

Case Example 12

A twenty-four year old woman volunteered to use 1 ml of a composition produced according to Example 2. Using a standardized consumer testing results questionnaire, she reported the following information: a) That sensation and sensitivity in her genital area seemed to be more than usual. b) That it was pleasurable and satisfying. c) That she first noticed the change in sensation in about two minutes. c) That the change in sensation lasted approximately forty-five minutes. d) That she experienced enhanced warmth and tingling. e) That after using the product, intercourse was more pleasurable and satisfying than normal. f) That her vaginal lubrication seemed to be the same as always. g) That her ability to achieve orgasm was unchanged. h) That the product enhanced her sexual experience and would like to continue using it. i) That she would purchase the product and use it on special occasions and when she needed a boost. j) That she did not experience any unpleasant or unwanted effects other than some minor burning.

Case Example 13

A forty-seven year old woman volunteered to use 1 ml of a composition produced according to Example 2. Using a standardized consumer testing results questionnaire, she reported the following information: a) That sensation and sensitivity in her genital area seemed to be more than usual. b) That it was pleasurable and satisfying. c) That she first noticed the change in sensation in about three minutes. c) That the change in sensation lasted approximately thirty minutes. d) That she experienced enhanced warmth, tingling and sensation. e) That after using the product, intercourse was more pleasurable and satisfying than normal. f) That her vaginal lubrication seemed to be the same as always. g) That her ability to achieve orgasm was unchanged. h) That the product enhanced her sexual experience and would like to continue using it. i) That she would purchase the product and use it routinely. j) That she did not experience any unpleasant or unwanted effects.

Case Example 14

A thirty year old woman volunteered to use 1 ml of a composition produced according to Example 2. Using a standardized consumer testing results questionnaire, she reported the following information: a) That sensation and sensitivity in her genital area seemed to be more than usual. b) That it was pleasurable and satisfying. c) That she first noticed the change in sensation in about four to five minutes. c) That the change in sensation lasted approximately one and one-half hours. d) That she experienced enhanced wetness, warmth, tingling, fullness (engorgement), sensation, arousal, orgasm, quicker to arousal and quicker to orgasm. e) That after using the product, intercourse was more pleasurable and satisfying than normal. f) That her vaginal lubrication seemed to be more than usual. g) That her ability to achieve orgasm was unchanged. h) That the product enhanced her sexual experience and would like to continue using it. i) That she would purchase the product and use it on special occasions. j) That she did not experience any unpleasant or unwanted effects.

Case Example 15

A twenty-five year old woman volunteered to use 0.5 ml of a composition produced according to Example 2. Using a standardized consumer testing results questionnaire, she reported the following information: a) That sensation and sensitivity in her genital area seemed to be more than usual. b) That it was pleasurable and satisfying. c) That she first noticed the change in sensation in about five minutes. c) That the change in sensation lasted approximately one hour. d) That she experienced enhanced warmth, tingling, sensation, arousal, orgasm and quicker to orgasm. e) That after using the product, intercourse was more pleasurable and satisfying than normal. f) That her vaginal lubrication seemed to be the same as always. g) That it was easier for her to achieve orgasm. h) That the product enhanced her sexual experience and would like to continue using it. i) That she would purchase the product and use it on special occasions and when she needed a boost. j) That she did not experience any unpleasant or unwanted effects.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius; and, unless otherwise indicated, all parts and percentages are by weight.

The entire disclosure of all applications, patents and publications, cited above, and of corresponding U.S. Provisional Application Ser. No. 60/214,472, filed Jun. 27, 2000, is hereby incorporated by reference.

The invention claimed is:

1. A method for improving female sexual arousal, treating female sexual arousal disorder, female orgasmic disorder, or female sexual pain disorder comprising:
    applying to the external female genitalia or vagina of a female in need thereof, a composition comprising:
    a therapeutically effective amount of gamma linolenic acid, a therapeutically effective amount of *Angelica* root, and a therapeutically effective amount of *Coleus forskohlii* extract.

2. The method of claim 1, wherein the gamma linolenic acid comprises 10% to 99% w/w of said composition.

3. The method of claim 1, wherein the gamma linolenic acid is from borage seed oil.

4. The method of claim 1, wherein the *Angelica* root comprises 0.001% to 99% w/w of the composition.

5. The method of claim 1, wherein the *Angelica* root is *Angelica pubescens*.

6. The method of claim 1, wherein the *Coleus forskohlii* comprises 0.001 to 8% w/w of the composition.

7. The method of claim 1, wherein the composition further comprises vinpocetine.

8. The method of claim 7, wherein the composition comprises 0.001% to 8% w/w vinpocetine.

9. The method of claim 1, wherein the composition further comprises a flavoring agent.

10. The method of claim 9, wherein the flavoring agent is a sweetening agent.

11. The method of claim 9, wherein the flavoring agent is selected from the group consisting of saccharin, monosodium guanosine mono phosphate, blackberry and lavender.

* * * * *

UNITED STATES PATENT AND TRADEMARK OFFICE
CERTIFICATE OF CORRECTION

| | | |
|---|---|---|
| PATENT NO. | : 7,875,299 B2 | Page 1 of 1 |
| APPLICATION NO. | : 10/834162 | |
| DATED | : January 25, 2011 | |
| INVENTOR(S) | : Crosby et al. | |

It is certified that error appears in the above-identified patent and that said Letters Patent is hereby corrected as shown below:

On the title page, item [60] should read as follows:

-- Provisional Appln. No. 60/214,472, filed June 27, 2000. --.

On the title page, item [63] should read as follows:

-- Continuation of Appln. No. 09/891,526, filed June 27, 2001, now U.S. Patent No. 6,737,084. --.

Col. 10, line 10, delete "mil" and substitute therefor -- ml --.

Signed and Sealed this
Eighth Day of March, 2011

David J. Kappos
*Director of the United States Patent and Trademark Office*